US00PP29989P3

(12) United States Plant Patent
Goffreda et al.

(10) Patent No.: US PP29,989 P3
(45) Date of Patent: Dec. 18, 2018

(54) PEACH TREE NAMED 'NJ357'

(50) Latin Name: ***Prunus persica* L.**
Varietal Denomination: NJ357

(71) Applicant: RUTGERS, THE STATE UNIVERSITY OF NEW JERSEY, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 67 days.

(21) Appl. No.: 15/530,545

(22) Filed: Jan. 26, 2017

(65) Prior Publication Data

US 2018/0213696 P1 Jul. 26, 2018

(51) Int. Cl.
*A01H 5/08* (2018.01)
*A01H 6/74* (2018.01)

(52) U.S. Cl.
USPC ..... Plt./198
CPC ..... *A01H 6/7463* (2018.05)

(58) Field of Classification Search
USPC ..... Plt./156, 180, 194, 198
See application file for complete search history.

(56) References Cited

PUBLICATIONS

Callahan Michigan Show Peach and Plum Great Lakes Expo, Plums, Pluots, Flat Peach, and Other Novel Stone Fruits Nov. 22, 2016, retrieved on May 1, 2018, retrieved from the Internet at www.glexpo.com/summaries/2016summaries/Peach-Plunn.pdf, 13 pp. (Year: 2016).*

* cited by examiner

*Primary Examiner* — Susan McCormick Ewoldt
*Assistant Examiner* — Karen M Redden
(74) *Attorney, Agent, or Firm* — Patrick J. Daugherty; Daugherty & Del Zoppo Co., L.P.A.

(57) ABSTRACT

A new and distinct peach variety of *Prunus persica* named 'NJ357' is provided. This variety is distinguished from other peach varieties by its unique combination of showy flowers, large, nearly round, freestone fruit, with an attractive red blush and orange-red mottle over a bright yellow-orange ground color, ripening in midseason, with yellow-orange, firm, juicy flesh, and sweet, subacid flavor that is maintained following cold storage.

6 Drawing Sheets

Latin name of genus and species of the plant claimed: *Prunus persica* L.
Variety denomination: 'NJ357'.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of peach tree named 'NJ357'. Our new tree resulted from crossing our proprietary peach seedling selection 'H15-20-90258' (non-patented) as the seed parent with 'Summerprince' (non-patented) peach tree, as the pollen parent. The new variety differs from seed parent 'H15-20-90258' in that the new variety produces viable pollen and has a more sweetness and aromatics. The new variety differs from pollen parent 'Summerprince' in that the new variety produces larger fruit that are sweet and lower acidity. The resulting tree was selected when growing in a cultivated area as the $47^{th}$ tree in the $7^{th}$ row of Block H at a fruit research farm in Cream Ridge, N.J.

BRIEF SUMMARY OF THE INVENTION

The 'NJ357' variety is distinguished from related cultivar 'Autumnglo' (unpatented), in that 'NJ357' fruit has a sweet, subacid flavor, and ripens in mid-season, whereas 'Autumnglo' fruit has an acidic flavor, and ripens about 4 weeks later. 'NJ357' differs from the related cultivar 'Encore' (U.S. Plant Pat. No. 4,572), in that 'NJ357' fruit has a sweet, subacid flavor, and ripens in mid-season, whereas 'Encore' fruit has an acidic flavor, and ripens about 4 weeks later. The 'NJ357' variety may also be distinguished from other peach varieties due to the following unique combination of characteristics:

- Nearly round fruit with a low tendency to split when adequately cropped.
- Large, yellow-orange fleshed fruit, with an attractive red blush and orange-red mottle over a bright yellow-orange ground color.
- Excellent production of firm fruit that ripen in midseason.
- Fruit with a good to very good eating quality and sweet, subacid flavor.

The variety was asexually reproduced at a fruit research farm in Cream Ridge, N.J. Asexual reproduction of this new variety by budding onto 'Lovell' peach seedling rootstock (non-patented) shows that the foregoing characteristics are so reproduced.

The following detailed description concerns the original tree, 'NJ357'. The original tree and asexual progeny have been observed growing in a cultivated area at the fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966)

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
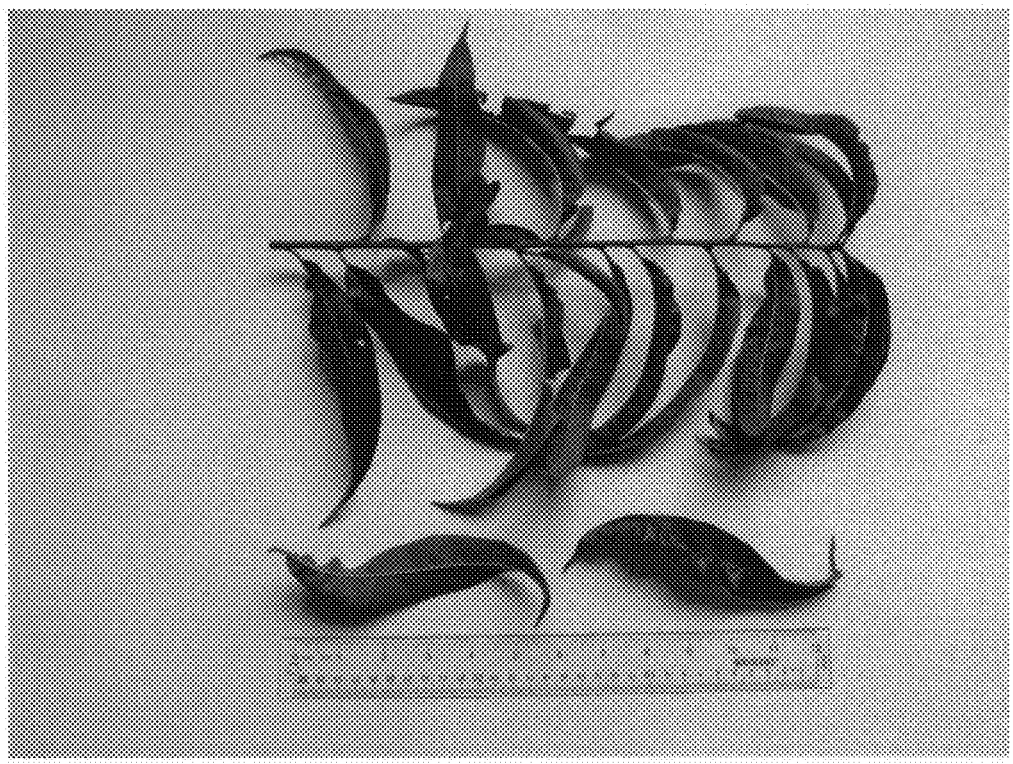
FIG. 1 is a color photograph taken on Aug. 22, 2014, of a characteristic twig of an approximately six (6) year old 'N1357' bearing typical leaves of the foliage.
Figure 2:
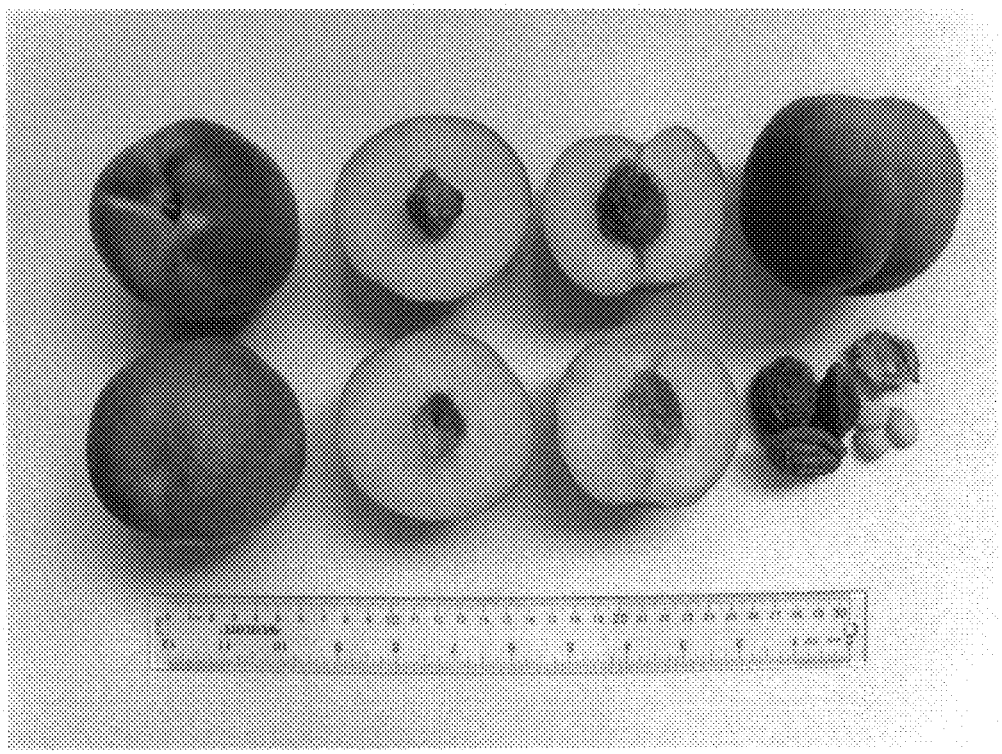
FIG. 2 is a color photograph taken on Aug. 11, 2014 of characteristic mature fruit and stones of an approximately six (6) year old 'NJ357'. Whole fruit are presented in three positions and both a transverse and longitudinal cross section to illustrate that the pericarp does not adhere to the pit when the fruit is mature. The stones exemplify the obovate shape and pits and grooves on the surface of the stone.
Figure 3:
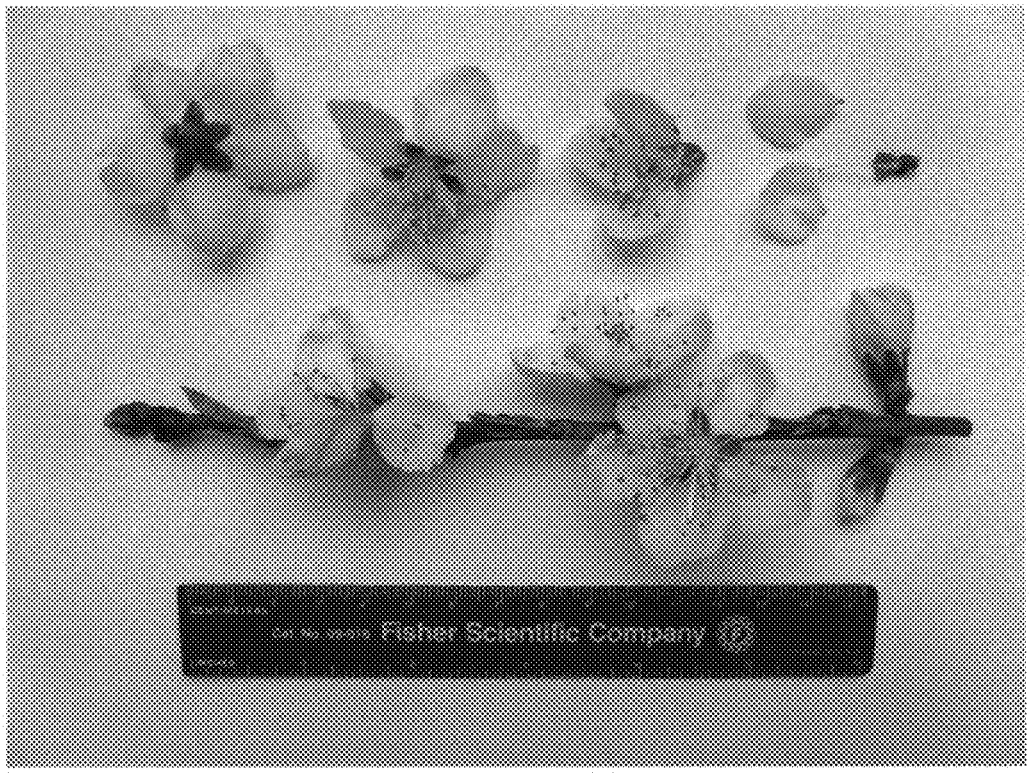
FIG. 3 is a color photograph of a characteristic twig that illustrates the typical flower buds and large, showy flowers of an approximately six (6) year old 'NJ357' observed on a tree at the fruit research farm in Cream Ridge, N.J. on Apr. 21, 2015.
Figure 4:
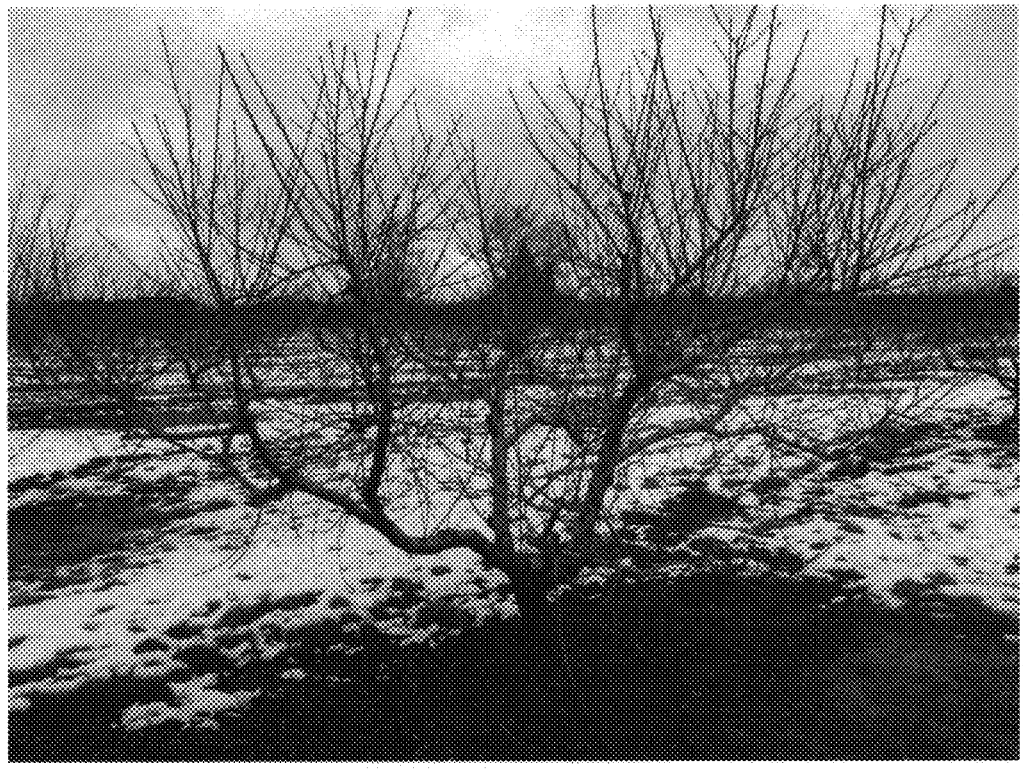
FIG. 4 is a color photograph of a an approximately six (6) year old dormant tree of 'NJ357', prior to pruning, in late winter that illustrates the spreading growth habit of a tree at the fruit research farm in Cream Ridge, N.J. on Feb. 8, 2016.
Figure 5:
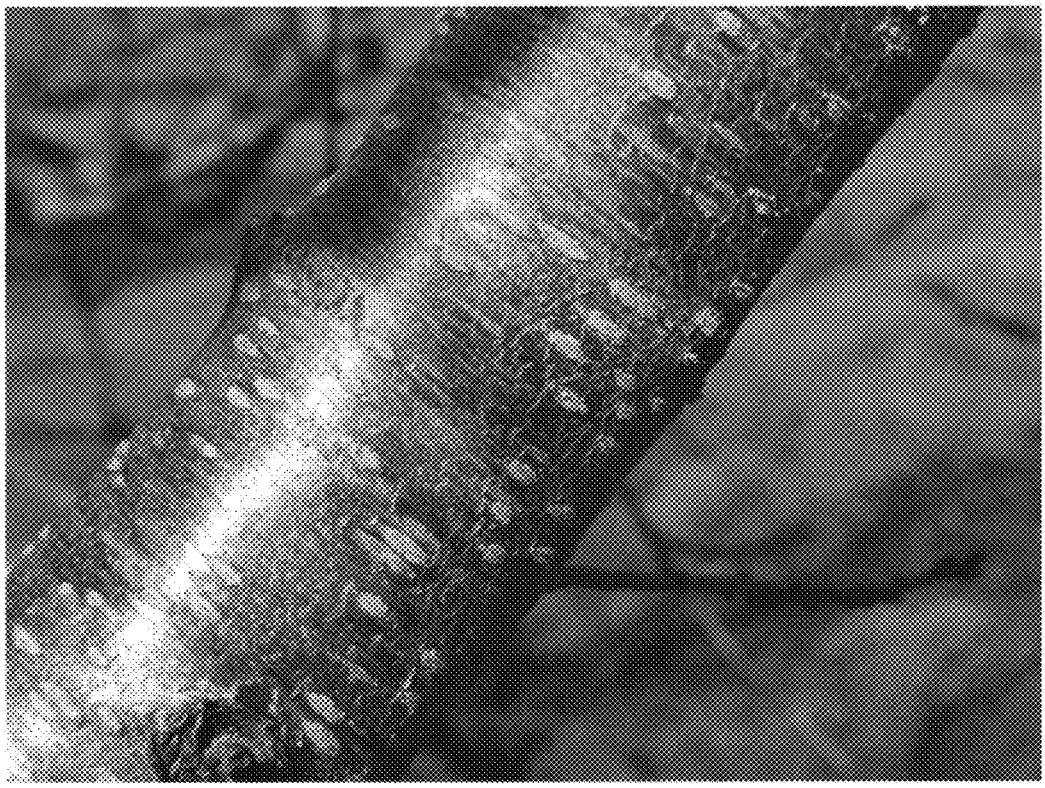
FIG. 5 is a color photograph taken on Mar. 17, 2015 of immature bark of an approximately six (6) year old 'NJ357' that illustrates color and the moderate density of conspicuous elliptic lenticels on the immature bark.
Figure 6:
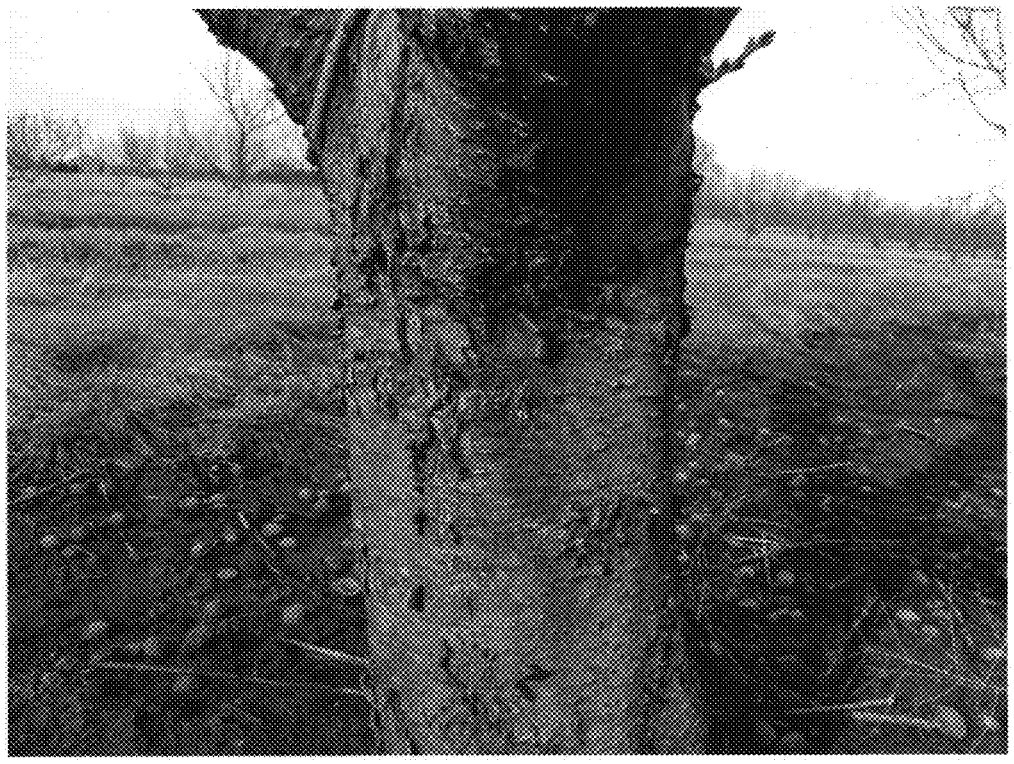
FIG. 6 is a color photograph taken on Mar. 11, 2015 of mature bark of an approximately six (6) year old 'NJ357' that illustrates the grey color, areas of shallow exfoliation, and slightly rough texture of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ357' variety is based on observations of an asexually reproduced tree. The observed tree was six years of age and growing on 'Lovell' seedling rootstock (non-patented) at said fruit research farm in Cream Ridge, N.J.

Scientific name: *Prunus persica* L.

Parentage:

*Seed parent*.—'H15-20-90258'. Pollen parent: 'Summerprince'.

Tree:

*Vigor*.—Vigorous.

*Plant hardiness zone*.—Growth of plants has only been observed in zone 6b.

*Dormant flower bud cold tolerance*.—At least to −20° C.

*Time of leaf bud burst*.—Typically in mid-April when grown in Cream Ridge, N.J., but can vary by one to two weeks.

*Overall shape*.—Spreading.

*Height*.—Average as compared to other peach cultivars. For example, measurement of a typical grafted tree on 'Lovell' peach seedling rootstock (non-patented) at six years after planting shows an average height of 3.4 meters when grown in Cream Ridge, N.J.

*Width*.—Average as compared to other peach cultivars. For example, measurement of a typical grafted tree on 'Lovell' peach seedling rootstock (non-patented) at six years after planting shows an average width of 4.3 meters when grown in Cream Ridge, N.J.

*Caliper*.—Six year old tree is 48 cm. in circumference measured at 20 cm. from the ground.

Trunk and branches:

*Trunk bark texture*.—Slightly rough with areas of shallow exfoliation.

*Trunk bark color*.—Grey (RHS 201C).

*Primary branches*.—Branches that are approximately 16 cm. in circumference are greyed-orange (RHS 176B) overlaid with grey (RHS 201B).

*Lenticels*.—Moderate density, approximately 1.1 per square cm; elliptical in shape and conspicuous; typical examples of which averaged 5.5 mm. in length and 2.2 mm. in width; grey (RHS 201D) in color becoming greyed-orange (RHS 174B) towards the center.

*Branch pubescence*.—None.

*New growth bark*.—Greyed-purple (RHS 183A) in sun; color yellow-green (RHS 152D) in shade overlaid with greyed-red (RHS 182b).

*Internodes*.—Length averaging 22.2 mm. on a one-year shoot.

Leaves:

*Texture*.—Glabrous, both surfaces

*Sheen*.—Young leaves semi-glossy with a flat finish on the underside.

*Length*.—About 165 mm. to 191 mm., averaging about 175 mm. including the petiole.

*Width*.—About 31 mm. to 37 mm., averaging about 35 mm.

*Petiole*.—Averaging 9.4 mm. long and about 2.0 mm. in diameter; Color yellow-green (146 B).

*Margin*.—Crenate.

*Margin undulation*.—Wavy.

*Form*.—Lanceolate, and concave in cross section.

*Apex*.—Sharply acuminate, curved downward.

*Base*.—Acute.

*Venation*.—Pinnate.

*Glands*.—Number: About 2 to 4, averaging about 2.7. Position: Mostly located on the petiole, occasionally on the leaf margin near its base. Size: Length averaging 1.6 mm. and width averaging 1.2 mm. Form: Reniform.

*Stipules*.—Stipules are present on immature leaves, but they are not persistent; typically, two per immature leaf, with an average length of 10.3 mm; color is yellow-green (RHS 146 B), becoming yellow-green (152 A) just prior to dehiscence. No stipules observed on mature leaves.

*Leaf color*.—Upper leaf surface: Yellow-green (between RHS 146A and RHS 147B). Lower leaf surface: Yellow-green (RHS 147B). Vein: Yellow-green (RHS 145C).

*Pubescence*.—None.

Flowers:

*Size*.—Large size, typical flower measuring between 39 mm. to 46 mm, averaging about 42 mm. across.

*Color*.—Dormant bud: Grey (RHS 201D) becoming Grey (RHS 201A) near the base. Pink stage bud: Red (between RHS 55A and RHS 55B). Open flower: Red (between RHS 55B and RHS 55D).

*Petals*.—Typically five petals per flower; slightly cupped, slightly elliptic to nearly round, with slight undulation at the margin, averaging about 21.3 mm. long and 17.6 mm. wide.

*Upper petal color*.—Red (between RHS 55B and RHS 55D).

*Lower petal color*.—Red (between RHS 55B and RHS 55D.

*Petal apex*.—Obtuse, nearly rounded.

*Petal base*.—Cuneate.

*Stamens*.—Position: perigynous and near the point of attachment of the petals. Number: Variable, typical range 40 and 48, averaging 43.4. Length: Variable, between 9.8 mm. to 16 mm, averaging 13.0 mm. Filament color: White (RHS 155C). Anther color: Orange-red (between RHS 34B and RHS 34C).

*Stigma*.—Located at approximately the same level as the majority of the stamens.

*Pistil*.—Number: One. Size: Length between 16 and 28 mm., averaging 20.1 mm. Pistil color: Yellow-green (RHS 145C). Ovary: Moderate, long pubescence and ellipsoid in shape, color yellow-green (RHS 145B).

*Sepals*.—Number: Five. Pubescence: Length short, heavy density. Color: Greyed-red (RHS 182C) to greyed-purple (RHS 183B) becoming greyed-green (RHS 146D) near the margin. Shape: Triangular, with a rounded apex; Size: Length averaging 6.6 mm, width averaging 4.3 mm.

*Nectar cup color*.—Greyed-orange (between RHS 169B and RHS 169C).

*Pollen*.—Abundant, tree produces viable pollen and is typically self-fruitful; yellow (RHS 11A) in color.

*Fragrance*.—Very slight.

*Bloom season*.—Onset of bloom in 2014 on April 16; full bloom on April 24.

Fruit:

*Size*.—Large, averaging about 7.2 cm. long, 7.5 cm. wide parallel to the suture and 6.9 cm. wide perpendicular to the suture.

*Typical weight*.—220 g.

*Form*.—Longitudinal section: Nearly round; slightly lipped at apex; Traverse section: Nearly round.

*Suture*.—Very shallow, extending from base to apex.

*Ventral surface*.—Nearly smooth at its base, becoming lipped towards the apex.

*Base*.—Flat.

*Apex*.—Flat to slightly depressed.

*Stem*.—Average length of 9.1 mm. and an average diameter of 4.3 mm.

*Skin*.—Thickness: Medium. Surface: Pubescent, generally light and short. Tenacity: Medium. Astringency: None. Tendency to crack: Low. Color: Blush is between red (RHS 46A) and greyed-purple (RHS 183A); mottle and stripes are orange-red (between RHS 34A and RHS 34B); ground color is yellow-orange (between RHS 21C and RHS 22D).

*Fruit properties*.—Flesh color: Yellow-orange (RHS 16C). Flesh adhesion: Freestone. Juice: Moderate. Firmness: above average. Texture: Firm, but melting. Fibers: Not noticeable. Ripens: Between July 25 and August 6 at Cream Ridge, N.J. Flavor: Sweet, subacid. Soluble solids: 11.7%. Aroma: Slight. Eating quality: Good to very good. Keeping quality: Medium. Has held its flavor and firmness for at least 14 days in cold storage at 1° C. to 2° C. May develop some inking after storage. Shipping quality: Good. No bruising or scaring disorders have been observed.

*Usage*.—Dessert.

*Market*.—Local and long distance.

*Productivity*.—Excellent, though varies greatly depending upon conditions inclusive of winter and spring temperatures, rainfall, tree density, pruning methods, soil type, fertilization, irrigation, and degree of fruit thinning. Trees have produced a full crop in 8 out of 10 years, and at least a partial crop in 9 out of 10 years at Cream Ridge, N.J.

Stone:

*Type*.—Freestone.

*Form*.—Obovate.

*Base*.—Medium.

*Apex*.—Narrow.

*Surface*.—Pits and grooves.

*Ventral suture*.—Medium to large.

*Dorsal ridge*.—Medium to high, broad width, forming deep lines.

*External color*.—Greyed-orange (RHS 165D).

*Cavity surface color*.—Greyed-orange (RHS 165D), mottled with greyed-orange (RHS 165C).

*Average stone dry weight*.—6.6 g.

*Average stone wall thickness*.—Varies between 5.3 mm. along the dorsal ridge to 9.4 mm. at the base.

*Size*.—Averages about 39.5 mm. long, 24.6 mm. wide parallel the dorsal ridge, and 19.9 mm. wide perpendicular to the dorsal ridge.

*Tendency to split*.—Typically low when well cropped.

Kernel:

*Form*.—Elliptic to slightly obovate.

*Skin color*.—Greyed-orange (between RHS 163B and RHS 163C).

*Vein color*.—Greyed-orange (RHS 163A).

*Viability*.—Yes, but may need to be germinated in tissue culture.

*Size*.—Averages about 17.1 mm. long, 11.7 mm. wide, and 1.8 mm. in breadth.

Plant/fruit disease and pest resistance/susceptibility: No atypical resistances/susceptibilities have been noted under normal cultural practices.

We claim:

1. A new and distinct variety of peach tree, substantially as herein shown and described.

* * * * *